United States Patent
McColl et al.

(10) Patent No.: US 8,545,693 B2
(45) Date of Patent: Oct. 1, 2013

(54) ANALYTE MEASURMENT METHOD AND SYSTEM

(75) Inventors: David McColl, Inverness (GB); Adam Craggs, Inverness (GB); Stephen MacKintosh, Inverness (GB); Steve Blythe, Inverness (GB); Marco Cardosi, Croy (GB)

(73) Assignee: LifeScan Scotland Limited

( * ) Notice: Subject to any disclaimer, the term of this patent is extended or adjusted under 35 U.S.C. 154(b) by 290 days.

(21) Appl. No.: 12/875,887

(22) Filed: Sep. 3, 2010

(65) Prior Publication Data

US 2011/0073494 A1    Mar. 31, 2011

Related U.S. Application Data

(60) Provisional application No. 61/246,858, filed on Sep. 29, 2009, provisional application No. 61/286,106, filed on Dec. 14, 2009.

(51) Int. Cl.
*G01N 33/50* (2006.01)
*C12Q 1/00* (2006.01)

(52) U.S. Cl.
USPC ............. 205/777.5; 204/400; 204/403.01; 204/403.04

(58) Field of Classification Search
USPC .......... 205/777.5; 204/400, 403.01–403.04
See application file for complete search history.

(56) References Cited

U.S. PATENT DOCUMENTS

| | | | |
|---|---|---|---|
| 4,731,726 A | 3/1988 | Allen | |
| 5,708,247 A | 1/1998 | McAleer et al. | |
| 5,951,836 A | 9/1999 | McAleer et al. | |
| 6,241,862 B1 | 6/2001 | McAleer et al. | |
| 6,475,372 B1* | 11/2002 | Ohara et al. | 205/777.5 |
| 7,112,265 B1 | 9/2006 | McAleer et al. | |
| 8,080,153 B2* | 12/2011 | Feldman et al. | 205/777.5 |
| 2005/0176153 A1 | 8/2005 | O'Hara et al. | |
| 2007/0231914 A1 | 10/2007 | Deng et al. | |
| 2008/0235053 A1 | 9/2008 | Ray et al. | |
| 2008/0312512 A1 | 12/2008 | Brukalo et al. | |
| 2009/0099509 A1 | 4/2009 | Estes et al. | |
| 2009/0105570 A1 | 4/2009 | Sloan et al. | |

(Continued)

FOREIGN PATENT DOCUMENTS

| | | |
|---|---|---|
| EP | 1338295 A1 | 8/2003 |
| EP | 1568310 A1 | 8/2005 |

(Continued)

OTHER PUBLICATIONS

STIC search: 12875887-397834-EICSEARCH.pdf.*

(Continued)

*Primary Examiner* — Luan Van
*Assistant Examiner* — Steven Rosenwald

(57) ABSTRACT

Described and illustrated herein are systems and exemplary methods of operating a multianalyte measurement system having a meter and a test strip. In one embodiment, the method may be achieved by applying a test voltage between a reference electrode and a first working electrode; measuring a first test current, a second test current and a third test current at the working electrode with the meter after a blood sample containing an analyte is applied to the test strip; estimating a hematocrit-corrected analyte concentration from the first, second and third test currents; and displaying the hematocrit-corrected analyte concentration.

3 Claims, 14 Drawing Sheets

(56) References Cited

U.S. PATENT DOCUMENTS

| | | |
|---|---|---|
| 2009/0112069 A1 | 4/2009 | Kanamori et al. |
| 2009/0156923 A1 | 6/2009 | Power et al. |
| 2009/0156924 A1 | 6/2009 | Shariati et al. |
| 2009/0184004 A1 | 7/2009 | Chatelier et al. |
| 2009/0237262 A1 | 9/2009 | Smith et al. |
| 2010/0041960 A1 | 2/2010 | Yuan |
| 2010/0174228 A1 | 7/2010 | Buckingham et al. |

FOREIGN PATENT DOCUMENTS

| | | |
|---|---|---|
| EP | 1 770 396 A2 * | 4/2007 |
| EP | 1770396 A1 | 4/2007 |
| EP | 1840219 A1 | 10/2007 |
| WO | WO 2008/073609 A2 | 6/2008 |

OTHER PUBLICATIONS

Clarke, William L., et al., *Evaluating Clinical Accuracy of Systems for Self-Monitoring Blood Glucose*, Diabetes Care, vol. 10 No. 5, 622-638 (1987).

Parkes, Joan L., et al., *New Consensus Error Grid to Evaluate the Clinical Significance of Inaccuracies in the Measurement of Blood Glucose*, Diabetes Care, vol. 23, No. 8, 1143-1147 (2000).

International PCT Patent Application No. PCT/US2010/040434, International Search Report, dated Oct. 20, 2010, 3 pgs, European Patent Office, Rijswijk.

International Search Report, PCT Application No. PCT/US2010/040383, dated Nov. 4, 2010, 3 pages, European Patent Office, Rijswijk.

International Search Report, PCT Application No. PCT/US2010/040425, Dated Dec. 23, 2010, 7 pages, European Patent Office, Rijswijk, Netherlands.

Partial International Search Report, Annex to Form PCT/ISA/206, PCT Application No. PCT/US2010/040309, Dated Nov. 29, 2010, 2 pages, European Patent Office, Rijswijk, Netherlands.

International Search Report, PCT Application No. PCT/GB2010/001683, Dated Dec. 22, 2010, 4 pages, European Patent Office, Rijswijk, Netherlands.

"Accu-Chek Complete Owner's Booklet", Roche Diagnostics, 2004, XP002636883, Retrieved from internet: URL:https://www.accu-chek.com/us/customer-care/downloads.html [retrieved May 12, 2011], p. 8, pp. 33-40, pp. 46 and 86.

International Search Report, PCT Application No. PCT/US2010/040443, dated May 17, 2011, 3 pages, European Patent Office, Rijswijk, NL.

* cited by examiner

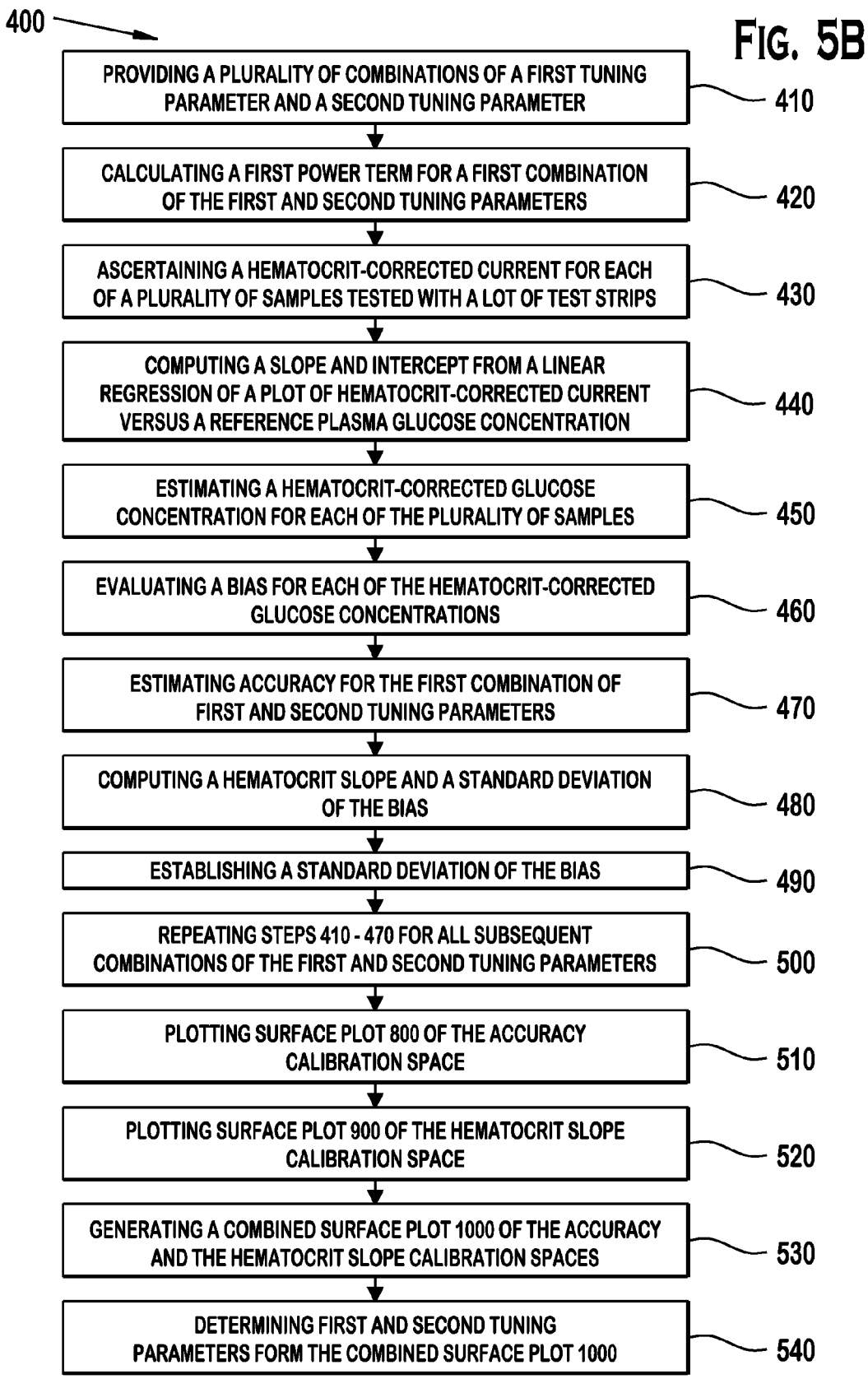

ANALYTE MEASURMENT METHOD AND SYSTEM

CROSS-REFERENCE

This application claims the benefits of priority under 35 USC§119 and/or §120 from prior filed U.S. Provisional Application Ser. Nos. 61/246,858, filed on Sep. 29, 2009, and 61/286,106, filed Dec. 14, 2009, which applications are incorporated by reference in their entirety into this application.

BACKGROUND

Electrochemical sensors have long been used to detect or measure the presence of substances in fluid samples. Electrochemical sensors include a reagent mixture containing at least an electron transfer agent (also referred to as an "electron mediator") and an analyte specific bio-catalytic protein (e.g. a particular enzyme), and one or more electrodes. Such sensors rely on electron transfer between the electron mediator and the electrode surfaces and function by measuring electrochemical redox reactions. When used in an electrochemical biosensor system or device, the electron transfer reactions are monitored via an electrical signal that correlates to the concentration of the analyte being measured in the fluid sample.

The use of such electrochemical sensors to detect analytes in bodily fluids, such as blood or blood derived products, tears, urine, and saliva, has become important, and in some cases, vital to maintain the health of certain individuals. In the health care field, people such as diabetics, for example, must monitor a particular constituent within their bodily fluids. A number of systems are capable of testing a body fluid, such as, blood, urine, or saliva, to conveniently monitor the level of a particular fluid constituent, such as, cholesterol, proteins, and glucose. Patients suffering from diabetes, a disorder of the pancreas where insufficient insulin production prevents the proper digestion of sugar, have a need to carefully monitor their blood glucose levels on a daily basis. Routine testing and controlling blood glucose for people with diabetes can reduce their risk of serious damage to the eyes, nerves, and kidneys.

Electrochemical biosensors may be adversely affected by the presence of certain blood components that may undesirably affect the measurement and lead to inaccuracies in the detected signal. This inaccuracy may result in an inaccurate glucose reading, leaving the patient unaware of a potentially dangerous blood sugar level, for example. As one example, the blood hematocrit level (i.e. the percentage of the amount of blood that is occupied by red blood cells) can erroneously affect a resulting analyte concentration measurement.

Variations in a volume of red blood cells within blood can cause variations in glucose readings measured with disposable electrochemical test strips. Typically, a negative bias (i.e., lower calculated analyte concentration) is observed at high hematocrit, while a positive bias (i.e., higher calculated analyte concentration) is observed at low hematocrit. At high hematocrit, for example, the red blood cells may impede the reaction of enzymes and electrochemical mediators, reduce the rate of chemistry dissolution since there is less plasma volume to solvate the chemical reactants, and slow diffusion of the mediator. These factors can result in a lower than expected glucose reading as less current is produced during the electrochemical process. Conversely, at low hematocrit, fewer red blood cells may affect the electrochemical reaction than expected, and a higher measured current can result. In addition, the blood sample resistance is also hematocrit dependent, which can affect voltage and/or current measurements.

Several strategies have been used to reduce or avoid hematocrit based variations on blood glucose. For example, test strips have been designed to incorporate meshes to remove red blood cells from the samples, or have included various compounds or formulations designed to increase the viscosity of red blood cell and attenuate the affect of low hematocrit on concentration determinations. Other test strips have included lysis agents and systems configured to determine hemoglobin concentration in an attempt to correct hematocrit. Further, biosensors have been configured to measure hematocrit by measuring optical variations after irradiating the blood sample with light, or measuring hematocrit based on a function of sample chamber fill time. These methods have certain disadvantages.

SUMMARY OF THE DISCLOSURE

Applicants have recognized a need for a system and method that can be used to determine an accurate glucose concentration that avoids the disadvantages in the field.

In view of the foregoing and in accordance with one aspect, there is provided a method of operating an analyte measurement system having a meter and a test strip. The test strip may include a reference electrode, a first working electrode and a second working electrode in which the first and second working electrodes are coated with a first and second reagent layer, respectively. The respective first and second reagent layers are disposed on a matrix layer having a mediator. The meter may include an electronic circuit for applying a test voltage between the reference electrode and the first working electrode and for applying a second test voltage between the reference electrode and the second working electrode. The meter also may include a signal processor for measuring a plurality of test currents and for calculating a glucose concentration from the test currents. The method may be achieved by applying a test voltage between the reference electrode and the second working electrode; measuring a first test current, a second test current and a third test current at the working electrode with the meter after a blood sample containing an analyte is applied to the test strip; ascertaining the glucose concentration from the first, second and third test currents; and displaying the glucose concentration.

In the exemplary method, the glucose concentration may be a value obtained with the following:

$$G = \frac{\left[\left(\frac{I_1}{I_2}\right)^p I_3\right] - \text{intercept1}}{\text{slope1}}$$

where:

G includes the hematocrit-corrected glucose concentration;

$I_1$ includes the first test current;

$I_2$ includes the second test current;

$I_3$ includes the third test current;

p includes a power term;

intercept1 includes an intercept value determined from a linear regression of a plot of $$\left[\left(\frac{I_1}{I_2}\right)^p I_3\right]$$

versus a reference glucose concentration; and
slope1 includes a slope value determined from a linear regression of a plot of $$\left[\left(\frac{I_1}{I_2}\right)^p I_3\right]$$

versus the reference glucose concentration.

In such embodiment, the power term p depends on a threshold value of the first test current $I_1$ and may be from about one to about four. If the first test current $I_1$ includes above the threshold value, then the above equation is used to calculate the hematocrit-corrected glucose concentration G. If the first test current $I_1$ is at or below the threshold value, then the power term p is set to zero in the above equation and the term $$\left(\frac{I_1}{I_2}\right)^p$$

becomes one. The threshold value of the first test current $I_1$ may be from about 4 microamperes to about 7 microamperes.

In another embodiment, the power term p may include a value obtained with the following:

$$p = a - \frac{b}{I_3}$$

where a includes a first tuning parameter and b includes a second tuning parameter.

In one embodiment, each of first and second tuning parameters a and b is from about zero to about five.

In another embodiment, batch-specific tuning parameters a and b may be determined by a calculating a first power term for a first combination of the first tuning parameter and the second tuning parameter with the following:

$$p1 = a - \frac{b}{I_3}$$

where p1 includes the first power term;
ascertaining the current for each of a plurality of samples tested with the batch of test strips with the following:

$$I_{corrected} = \left(\frac{I_1}{I_2}\right)^{p1} * I_3$$

where $I_{corrected}$ includes the hematocrit-corrected current;
computing a slope and intercept from a linear regression of a plot of hematocrit-corrected current versus a reference plasma glucose concentration;
estimating a hematocrit-corrected glucose concentration for each of the plurality of samples with the following:

$$G_{corrected} = \frac{I_{corrected} - \text{intercept2}}{\text{slope2}}$$

where $G_{corrected}$ includes the hematocrit-corrected glucose concentration, intercept2 includes an intercept value determined from a linear regression of a plot of $I_{corrected}$ versus a reference glucose concentration and slope2 includes a slope value determined from a linear regression of a plot of $I_{corrected}$ versus a reference glucose concentration;
evaluating a bias for each of the hematocrit-corrected glucose concentrations with equations of the form:

$$Bias_{abs} = G_{corrected} - G_{reference} \text{ for } G_{reference} \text{ less than 75 mg/dL and}$$

$$Bias_\% = \frac{G_{corrected} - G_{reference}}{G_{reference}} \text{ for } G_{reference} \text{ greater than or equal to 75 mg/dL}$$

where $Bias_{abs}$ includes absolute bias, $Bias_\%$ includes percent bias and $G_{reference}$ includes the reference glucose concentration;
estimating accuracy for the first combination of the first and second tuning parameters with the following:

$$\text{Accuracy} = \frac{n15}{n} * 100$$

where n15 includes the number of data points within a bias criteria and n includes the total number of data points;
computing a hematocrit slope from a linear regression of a plot of the bias versus the percent hematocrit;
establishing a standard deviation of the bias with the following:

$$s = \left(\frac{1}{n-1} \sum_{i=1}^{n} (x_i - \bar{x})^2\right)^{1/2}$$

where s includes the standard deviation, n includes the number of samples, $x_i$ includes the sample and $\bar{x}$ includes the mean of the sample;
repeating the previous steps for all combinations of the first and second tuning parameters; plotting an accuracy calibration space of the accuracy calibration space for all combinations of the first and second tuning parameters; plotting an accuracy calibration space of the hematocrit slope calibration space for all combinations of the first and second tuning parameters; generating a combined surface plot for all combinations of the first and second tuning parameters which meet an accuracy and hematocrit slope acceptance criteria; and determining batch-specific first and second tuning parameters from the combined surface plot.

In another embodiment, the method of determining batch-specific tuning parameters further may include determining a set of batch-specific calibration parameters, e.g., slope and intercept.

In yet another embodiment, the method of determining batch-specific tuning parameters further may include determining tuning parameters for multiple batches of test strips and then determining regions of overlap for all the batches in the combined surface plots of the accuracy calibration space and the hematocrit slope calibration space.

In yet a further embodiment, a method for determining a hematocrit-corrected test current measurable with a system having a test strip and a meter is provided. The method can be achieved by applying a test voltage between a reference electrode and a working electrode coated with a reagent layer disposed on a matrix layer having a mediator; measuring a first test current, a second test current and a third test current at the working electrode with the meter after a blood sample containing an analyte is applied to the test strip; and ascertaining a hematocrit-corrected test current via a ratio of the first test current to the second test current raised to a power term and multiplying the ratio by the third test current, in which the power term is a function of a first tuning parameter and a second tuning parameter.

In yet a further embodiment, an analyte measurement system to measure at least glucose concentration in physiological fluid of a user is provided. The system includes a test strip and a meter. The test strip includes a substrate having a reference electrode and a working electrode coated with a reagent layer, which is disposed on a matrix layer having a mediator. The electrodes are connected to corresponding contact pads. The analyte meter has a test circuit in connection with a test strip port that receives the contact pads of the test strip so that the meter is configured to apply a test voltage after deposition of physiological fluid on the electrodes and determine a hematocrit-corrected the glucose concentration from measured first, second and third test currents at first, second, and third discrete intervals after application of the test voltage by the meter.

These and other embodiments, features and advantages of the invention will become apparent to those skilled in the art when taken with reference to the following more detailed description of the exemplary embodiments in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (in which like numerals represent like elements), of which:

FIG. 5B illustrates a method to determine batch-specific first and second tuning parameters in the embodiments herein;

DETAILED DESCRIPTION OF ILLUSTRATIVE EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

Figure 1:
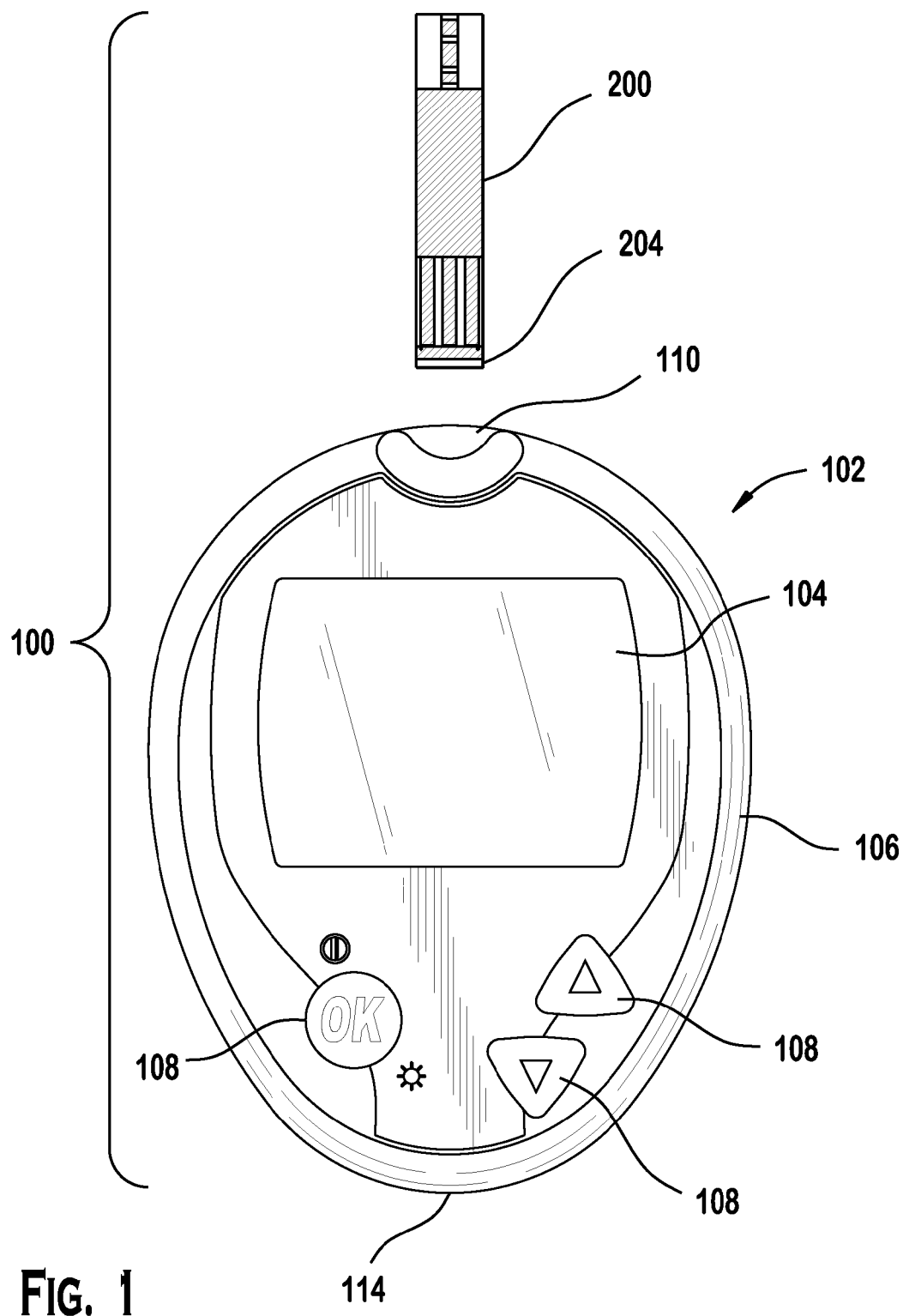
FIG. 1 illustrates an exemplary embodiment of a top view of a system for measuring two analyte concentrations.

FIG. 1 illustrates a system 100 for measuring at least two analyte concentrations in which system 100 may include a meter 102 and a test strip 200. Meter 102 may include a display 104, a housing 106, a plurality of user interface buttons 108, and a strip port 110. Meter 102 further may include electronic circuitry within housing 106 such as a memory 120, a microprocessor 122, electronic components for applying a test voltage, and also for measuring at least two test current values. A proximal portion 204 of test strip 200 may be inserted into strip port 110. Display 104 may output at least two analyte concentrations, e.g., glucose and/or a ketone concentration, and may be used to show a user interface for prompting a user on how to perform a test. The plurality of user interface buttons 108 allow a user to operate meter 102 by navigating through the user interface software. Display 104 may optionally include a backlight.

An optional data port 114 accepts a suitable connector attached to a connecting lead, thereby allowing meter 102 to be linked to an external device such as a personal computer. Data port 114 may be any port that allows for transmission of data (serial or parallel) such as, for example, serial or parallel port in wired or wireless form. A personal computer, running appropriate software, allows entry and modification of set-up information (e.g. the current time, date, and language), and may perform analysis of data collected by meter 102. In addition, the personal computer may be able to perform advanced analysis functions, and/or transmit data to other computers (i.e. over the internet) for improved diagnosis and treatment. Connecting meter 102 with a local or remote computer facilitates improved treatment by health care providers.

Figure 2:
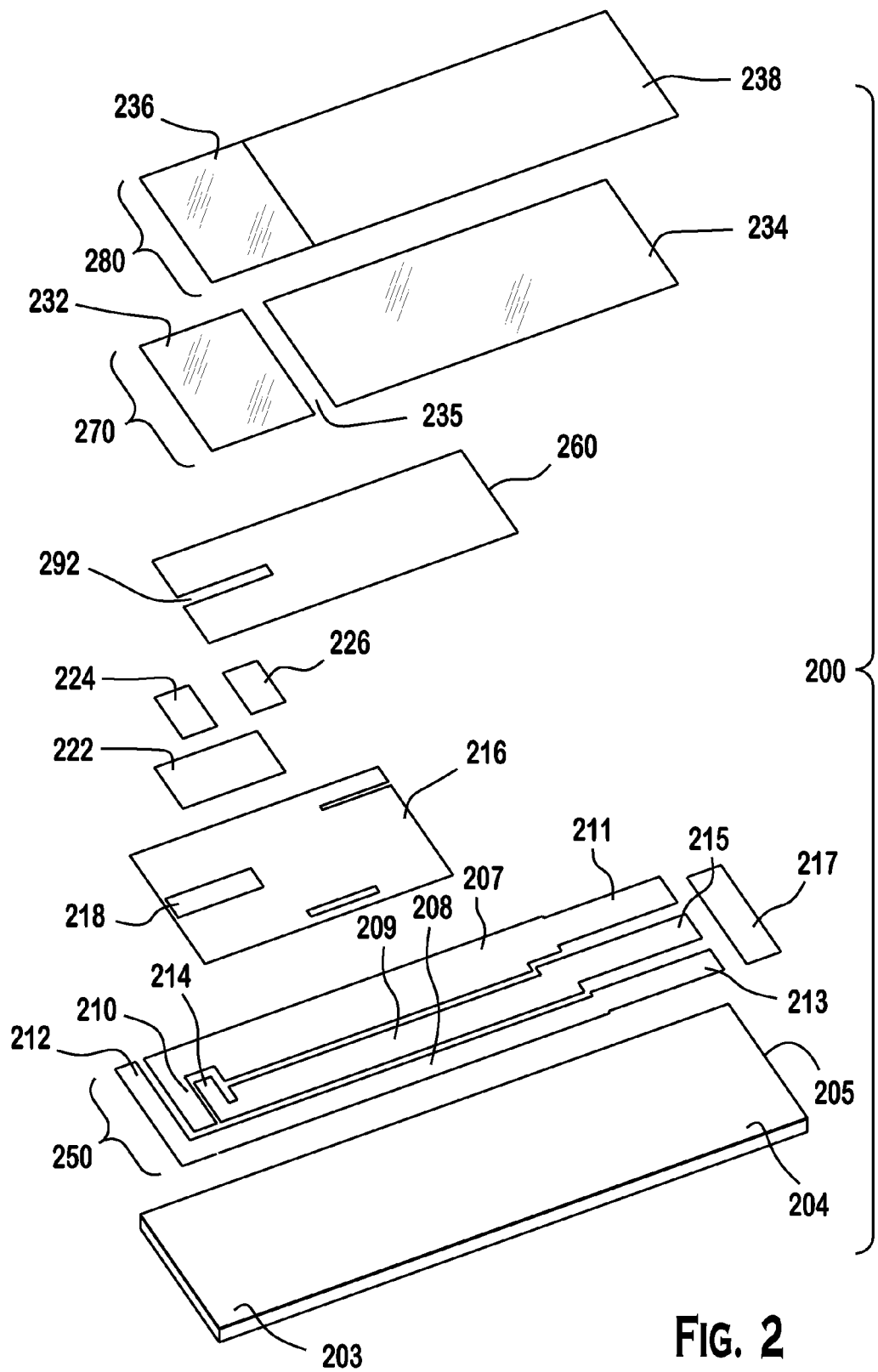
FIG. 2 illustrates an exemplary embodiment of a perspective exploded view of a test strip.
Figure 3:
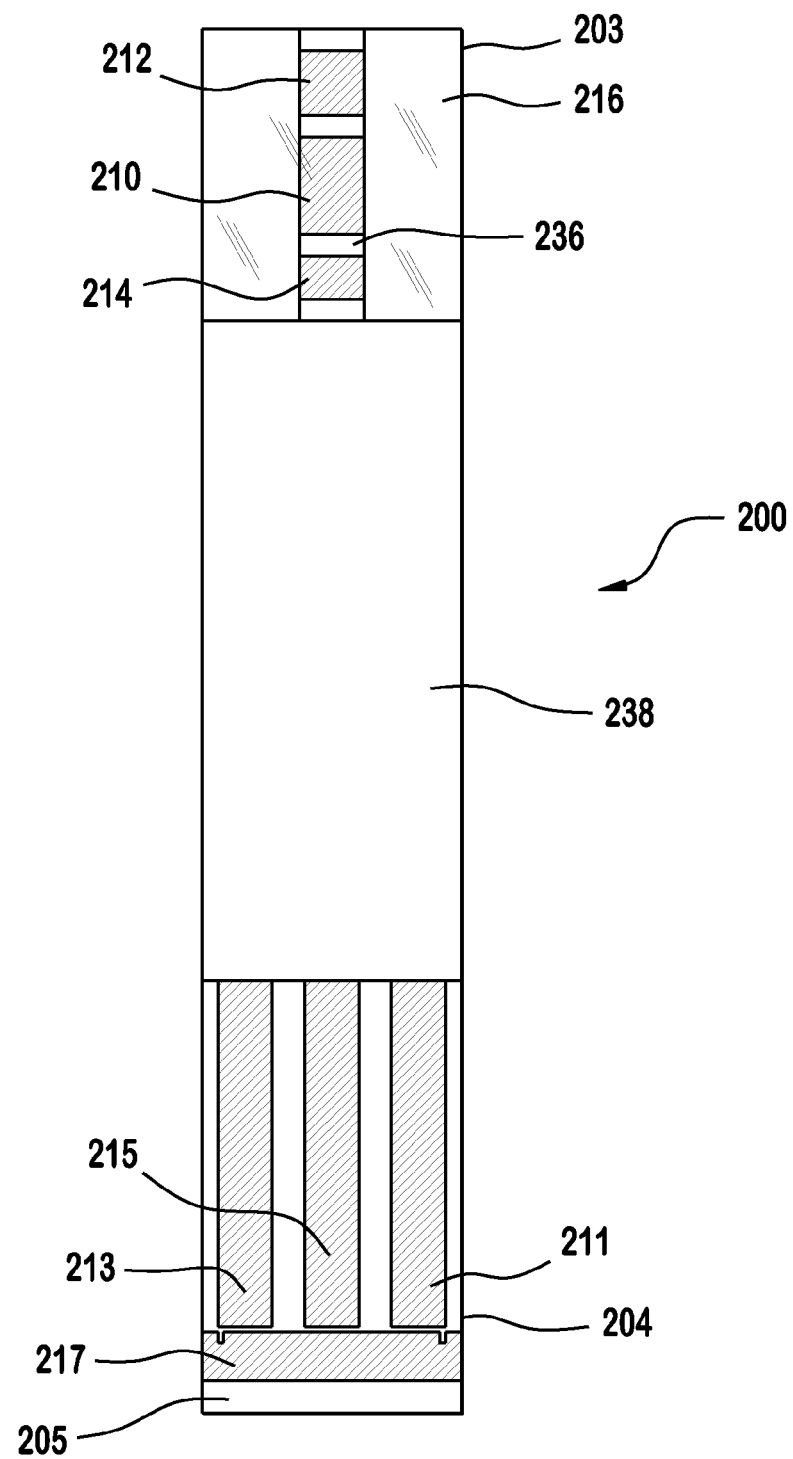
FIG. 3 illustrates an exemplary embodiment of a top view of the test strip shown in FIG. 2.

FIGS. 2 and 3 are exemplary exploded perspective and top assembled views, respectively, of test strip 200, which may include seven layers disposed on a substrate 205. The seven layers disposed on substrate 205 may be a conductive layer 250, an insulation layer 216, a matrix layer 222, a first reagent layer 224 and a second reagent layer 226, an adhesive layer 260, a hydrophilic layer 270, and a top layer 280. Test strip 200 may be manufactured in a series of steps where the conductive layer 250, insulation layer 216, matrix layer 222, first reagent layer 224, second reagent layer 226 and adhesive layer 260 are sequentially deposited on substrate 205 using, for example, a screen-printing process. Hydrophilic layer 270 and top layer 280 may be disposed from a roll stock and laminated onto substrate 205 as either an integrated laminate or as separate layers. Test strip 200 has a distal portion 203 and a proximal portion 204, as shown in FIG. 2.

Test strip 200 may include a sample-receiving chamber 292 through which a blood sample may be drawn. Sample-receiving chamber 292 may include an inlet at a proximal end of test strip 200. An outlet or air vent is included in hydrophilic layer 270, as will be described below. A blood sample may be applied to the inlet to fill a sample-receiving chamber 292 so that at least two analyte concentrations may be measured. The side edges of a cut-out portion of adhesive layer 260 located adjacent to first and second reagent layers 224 and 226 define a wall of sample-receiving chamber 292, as illustrated in FIG. 2. A bottom portion or "floor" of sample-receiving chamber 292 may include a portion of substrate 205, conductive layer 250, and insulation layer 216. A top portion or "roof" of sample-receiving chamber 292 may include distal hydrophilic portion 232.

For test strip 200, as illustrated in FIG. 2, substrate 205 may be used as a foundation for helping support subsequently applied layers. Substrate 205 may be in the form of a polyester sheet such as a polyethylene tetraphthalate (PET) material. Substrate 205 may be in a roll format, nominally 350 microns thick by 370 millimeters wide and approximately 60 meters in length.

A conductive layer is required for forming electrodes that may be used for the electrochemical measurement of glucose. Conductive layer 250 may be made from a carbon ink that is screen-printed onto substrate 205. In a screen-printing process, carbon ink is loaded onto a screen and then transferred through the screen using a squeegee. The printed carbon ink may be dried using hot air at about 140° C. The carbon ink may include VAGH resin, carbon black, graphite, and one or more solvents for the resin, carbon and graphite mixture. More particularly, the carbon ink may incorporate a suitable ratio of carbon black:VAGH resin in the carbon ink.

For test strip 200, as illustrated in FIG. 2, conductive layer 250 may include a reference electrode 210, a first working electrode 212, a second working electrode 214, a reference contact pad 211, a first contact pad 213, a second contact pad 215, a reference electrode track 207, a first working electrode track 208, a second working electrode track 209, and a strip detection bar 217. In the embodiment shown in FIG. 2, reference electrode 210 is located in between first working electrode 212 and second electrode 214 such that cross-talk between first and second working electrodes 212 and 214 is minimized.

Conductive layer 250 may be formed from a carbon ink. Reference contact pad 211, first contact pad 213 and second contact pad 215 may be configured to electrically connect to a test meter. Reference electrode track 207 provides an electrically continuous pathway from reference electrode 210 to reference contact pad 211. Similarly, first working electrode track 208 provides an electrically continuous pathway from first working electrode 12 to first contact pad 213. Similarly, second working electrode track 209 provides an electrically continuous pathway from second working electrode 214 to second contact pad 215. Strip detection bar 217 is electrically connected to reference contact pad 211. A test meter may detect that test strip 200 has been properly inserted by measuring a continuity between reference contact pad 211 and strip detection bar 217.

Insulation layer 216 may include a rectangular aperture 218 that exposes a portion of reference electrode 210, first working electrode 212, and second working electrode 214, which may be wetted by a liquid sample. The area of first working electrode 212, second working electrode 214, and reference electrode 210 may be defined as the area exposed to the liquid sample. In addition to defining an electrode area, insulation layer 216 prevents a liquid sample from touching the electrode tracks 207, 208, and 209. It is believed that the functional area of a working electrode should be accurately defined because the magnitude of the test current is directly proportional to the effective area of the electrode. As an example, insulation layer 216 may be Ercon E6110-116 Jet Black Insulayer™ ink that may be purchased from Ercon, Inc. The test strip at this point may be treated with plasma. The plasma is created by high-voltage alternating current (AC) between two or more plasma sources spaced about 100 millimeters apart and rotated about a generally vertical axis at ambient temperatures to define a plasma ring. The plasma ring is configured to be spaced apart from the substrate 205, which may include the test strip electrode, at a distance of approximately 5 millimeters to approximately 30 millimeters and preferably from about 10 millimeters to about 20 millimeters. The voltage utilized by the plasma controller may be configured to be about 5 kVA and the voltage provided to the plasma electrodes is preferably less than about 2 kVA. The frequency of the AC is about 16 kHz to about 20 kHz. The resulting ring of plasma, consisting of ionised, highly energetic particles is swept downstream towards the substrate 205 using filtered and generally contaminant free compressed air at about 1.2 bars or higher absolute pressure, preferably about 2.5 bars at a volumetric flow rate of less than 2 cubic meter of air per hour, towards the substrate 205, which may be moving orthogonally to the flow of air at about 5 meters per minute to about 15 meters per minute and preferably approximately 10 meters per minute. The plasma ring may be arrayed adjacent to other plasma rings along the path of travel of the substrates. The number of plasma rings may be from one to as many as necessary along the path of travel of the substrate or transverse to such path to provide for surface modification of the substrate. The plasma is used to modify the surface of the screen printed carbon based electrodes. This surface modification or plasma treatment is believed to increase the electrochemical activity of the carbon surface and increase the surface energy of the printed layers allowing for better adhesion between them and subsequently printed layers. Plasma treatment is also believed to improve the electrochemistry of the carbon surface making the reaction with the mediator more ideal.

Matrix layer 222 may include a mediator such as, for example, ferricyanide and a cofactor such as, for example, nicotinamide adenine dinucleotide (NADH). In one embodiment, matrix layer 222 may include potassium ferricyanide, NADH, Tris-HCL buffer, hydroxyethylcellulose, DC 1500 Antifoam, Cabosil TS 610, poly (vinyl pyrrolidone vinyl acetate), Triton X-100, calcium chloride and analar water.

First and second reagent layers 224 and 226 are each disposed on matrix layer 222, as illustrated in FIG. 2. First and second reagent layers 224 and 226 each may include chemicals such as an enzyme which selectivity reacts with an analyte of interest such that the analyte concentration may be determined. The reagent layer can include an enzyme and a mediator. Exemplary enzymes suitable for use in the reagent layer include glucose oxidase, glucose dehydrogenase (with pyrroloquinoline quinone co-factor, "PQQ"), and glucose dehydrogenase (with flavin adenine dinucleotide co-factor, "FAD"). An exemplary mediator suitable for use in the reagent layer includes ferricyanide, which in this case is in the oxidized form. The reagent layer can be configured to physically transform glucose into an enzymatic by-product and in the process generate an amount of reduced mediator (e.g., ferrocyanide) that is proportional to the glucose concentration. The working electrode can then measure a concentration of the reduced mediator in the form of a current. In turn, glucose meter 102 can convert the current magnitude into a glucose concentration.

Exemplary analytes of interest for monitoring diabetes include glucose and ketones. In one embodiment, first reagent layer 224 may include at least one enzyme that selectively reacts with ketones and second reagent layer 226 may include an enzyme that selectively reacts with glucose. In another embodiment, first reagent layer 224 may include an enzyme that selectively reacts with glucose and second reagent layer 226 may include at least one enzyme that selectively reacts with ketones.

In one embodiment, the components in the reagent layer used to determine the ketone concentration may include beta-hydroxybutyrate dehydrogenase (BHD), Tris-HCL buffer, hydroxyethylcellulose, potassium ferricyanide, DC 1500 Antifoam, Cabosil TS 610, poly(vinyl pyrrolidone vinyl acetate), Triton X-100, calcium chloride and analar water. In another embodiment, the reagent layer used to measure ketones may include a second enzyme such as, for example, diaphorase Examples of enzymes suitable for use in the reagent layer for measuring glucose may include either glucose oxidase or glucose dehydrogenase. More specifically, the glucose dehydrogenase may have a pyrrylo-quinoline quinone (PQQ) cofactor or a flavin adenine dinucleotide (FAD) cofactor. In one embodiment, the components in the reagent layer that is used to determine the glucose concentration may include glucose oxidase, Tris-HCL buffer, hydroxyethylcellulose, potassium ferricyanide, DC 1500 Antifoam, Cabosil TS 610, poly(vinyl pyrrolidone vinyl acetate), Triton X-100, calcium chloride and analar water.

First and second reagent layers 224 and 226 may be formed from a reagent ink, which is disposed onto matrix layer 222 and dried. Note that the reagent ink may also be referred to as an enzyme ink or reagent formulation. A reagent ink typically contains a liquid, such as a buffer, for dispersing and/or dissolving materials used for the electrochemical detection of an analyte such as glucose. In one embodiment, first and second reagent layers 224 and 226 may be screen-printed in two successive steps onto matrix layer 222. Reagent ink may be loaded onto a screen until it is flooded. Next, a squeegee may be used to transfer the reagent ink through the screen and onto matrix layer 222. After the deposition, the reagent ink may be dried using hot air at about 50° C.

In one embodiment, the area of first reagent layer 224 and second reagent layer 226 is sufficiently large to cover the entire area of first working electrode 212 and second working electrode 214, respectively. Each of first and second reagent layers 224 and 226 include a width and a length that is sufficiently large to at least account for the largest electrode area that may be used in test strip 200. The width of first and second reagent layers 224 and 226 may be about 2 millimeters, which is more than double a width of rectangular aperture 218.

Adhesive layer 260 may be disposed on test strip 200 after the deposition of first and second reagent layers 224 and 226. Portions of adhesive layer 260 may be aligned to be immediately adjacent to, touch, or partially overlap with first and second reagent layers 224 and 226. Adhesive layer 260 may include a water based acrylic copolymer pressure sensitive adhesive which is commercially available. Adhesive layer 260 is disposed on a portion of insulation layer 216, conductive layer 250, and substrate 205. Adhesive layer 260 binds hydrophilic layer 270 to test strip 200.

Hydrophilic layer 270 may include a distal hydrophilic portion 232 and proximal hydrophilic portion 234, as illustrated in FIG. 2. A gap 235 is included between distal hydrophilic portion 232 and proximal hydrophilic portion 234. Gap 235 serves as a side vent for air as blood fills sample-receiving chamber 292. Hydrophilic layer 270 may be a polyester having one hydrophilic surface such as an anti-fog coating, which is commercially available from 3M.

The final layer to be added to test strip 200 is top layer 280, as illustrated in FIG. 2. Top layer 280 may include a clear portion 236 and opaque portion 238. Top layer 280 is disposed on and adhered to hydrophilic layer 270. Top layer 280 may be a polyester that has an adhesive coating on one side. It should be noted that the clear portion 236 substantially overlaps distal hydrophilic portion 232, which allows a user to visually confirm that sample-receiving chamber 292 may be sufficiently filled. Opaque portion 238 helps the user observe a high degree of contrast between a colored fluid such as, for example, blood within sample-receiving chamber 292 and opaque portion 238.

In another embodiment, the system may include a meter and test strip for measuring one analyte, e.g., glucose, as is described in U.S. Pat. Nos. 5,708,247, 5,951,836, 6,241,862, and 7,112,265, each of which is fully incorporated herein by reference.

Figure 4:
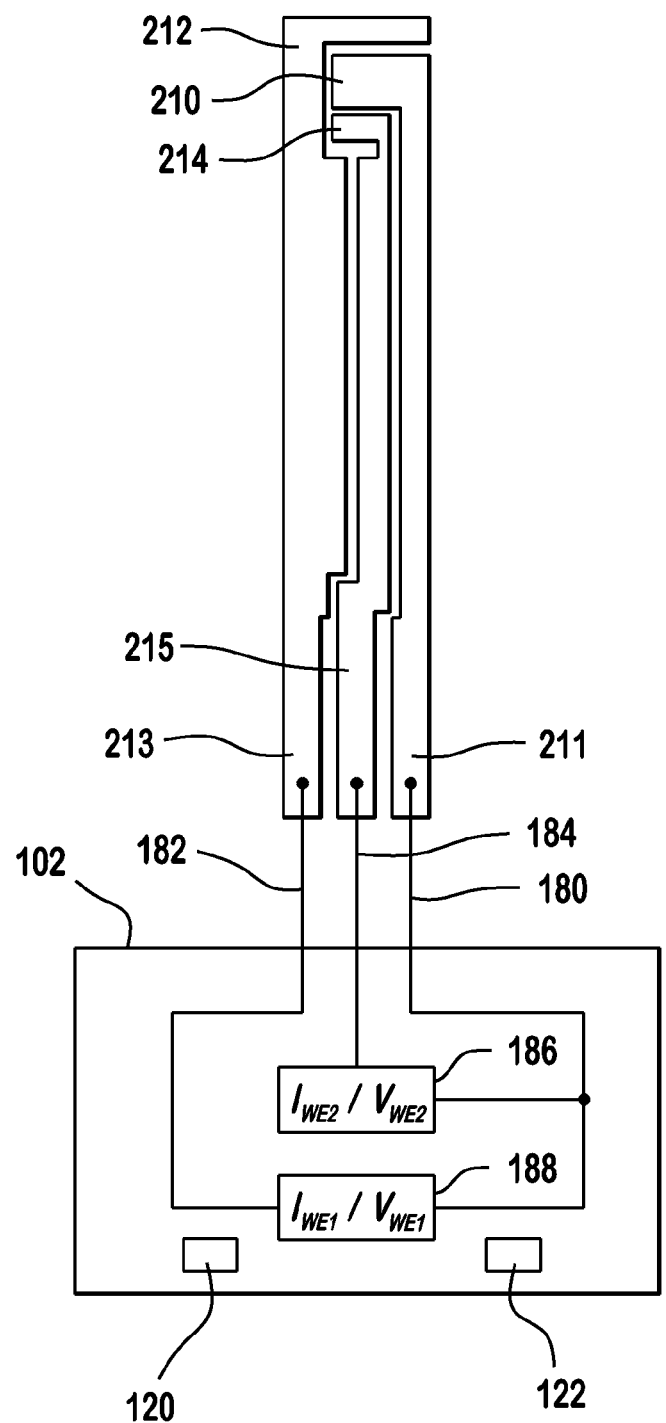
FIG. 4 illustrates an exemplary embodiment of a schematic of the functional components of the meter shown in FIG. 1 forming an electrical connection with the test strip of FIGS. 2 and 3.

FIG. 4 shows a simplified schematic of meter 102 interfacing with test strip 200. Meter 102 may include a reference connector 180, a first connector 182 and a second connector 184, which respectively form an electrical connection to reference contact 211, first contact 213 and second contact 215. The three aforementioned connectors are part of strip port 110. When performing a test, a first test voltage source 186 may apply a test voltage $V_{WE2}$ between second working electrode 214 and reference electrode 210. As a result of test voltage $V_{WE2}$, meter 102 may then measure a test current $I_{WE2}$ at second working electrode. In a similar manner, a second test voltage source 188 applies a test voltage $V_{WE1}$ between first working electrode 212 and reference electrode 210. As a result of test voltage $V_{WE1}$, meter 102 may then measure a test current $I_{WE1}$. In an embodiment, test voltage $V_{WE2}$ and second test voltage $V_{WE1}$ may be about equal. For simplifying the description of the following sections, the set of instructions for determining a hematocrit corrected glucose concentration will be described for only one working electrode and reference electrode. It should be apparent that the embodiments should not be limited to one working electrode and reference electrode, but that multiple working electrodes may also be utilized.

Figure 5A:
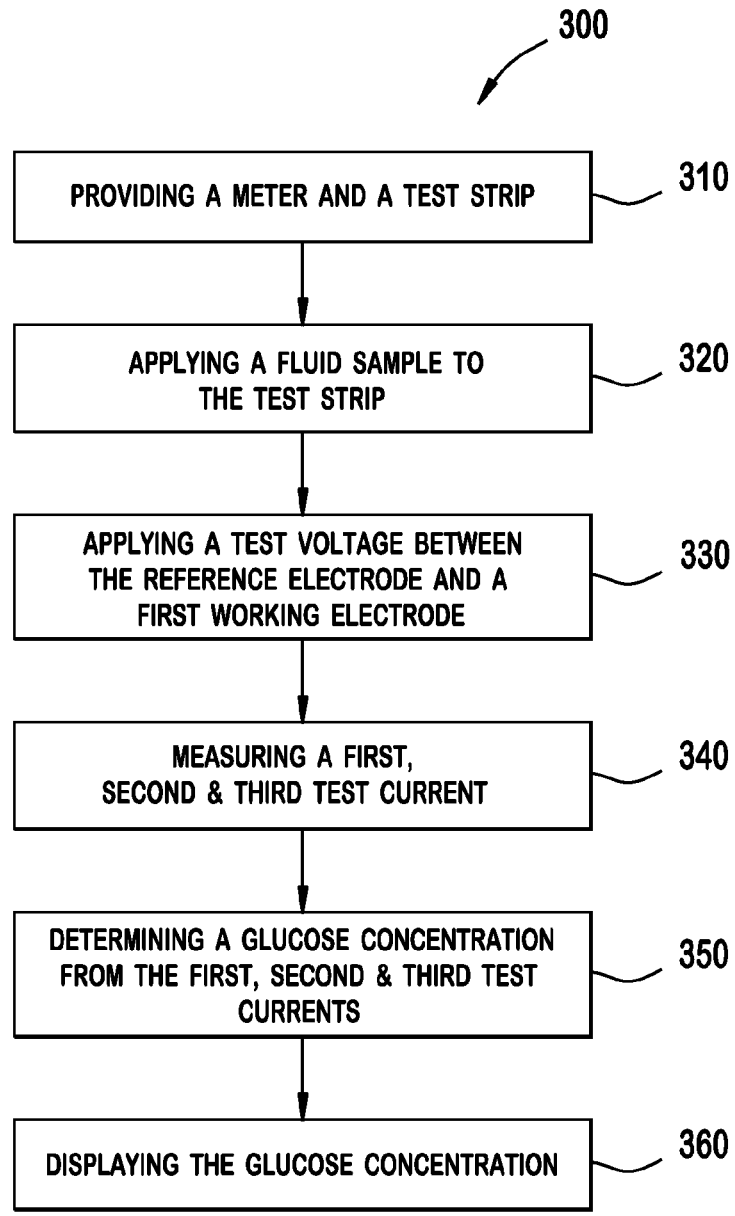
FIG. 5A illustrates an exemplary embodiment of a flow chart of a method of estimating a hematocrit-corrected glucose concentration using the system shown in FIG. 1

Referring to FIG. 5A, a method 300 for determining a hematocrit-corrected analyte concentration (e.g., glucose) that uses the aforementioned meter 102 and test strip 200 embodiments will now be described.

In exemplary step 310, meter 102 and test strip 200 are provided. Meter 102 may include electronic circuitry that can be used to apply at least one test voltage to the test strip and to measure current flowing through at least second working electrode 214. Meter 102 also may include a signal processor with a set of instructions for the method of determining at least one analyte concentration in a fluid sample as disclosed herein. In one embodiment, the analytes are blood glucose and ketone.

Figure 6:
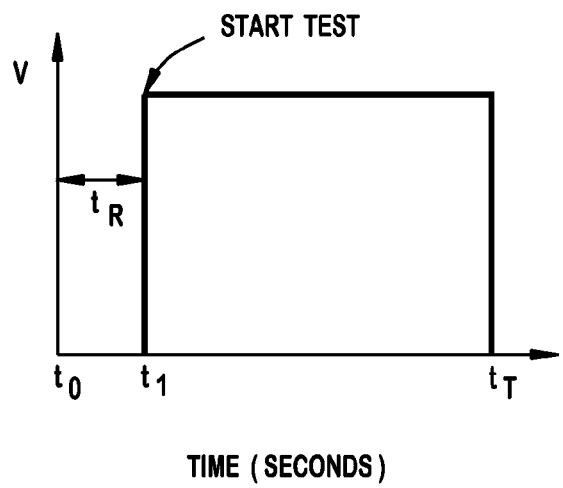
FIG. 6 illustrates an exemplary embodiment of a chart showing test voltages applied by the meter to the test strip.

FIG. 6 is an exemplary chart of a test voltage applied to test strip 200. Before a fluid sample is applied to test strip 200, test meter 102 is in a fluid detection mode in which a test voltage of about 400 millivolts is applied between second working electrode 214 and reference electrode 210. In exemplary step 320, the fluid sample is applied to test strip 100 at $t_0$ and is allowed to react with first and second reagent layers 224 and 226 for a reaction period $t_R$. The presence of sample in the reaction zone of test strip 200 is determined by measuring the current flowing through second working electrode 214. The beginning of reaction period $t_R$ is determined to begin when the current flowing through second working electrode 214 reaches a desired value, typically about 0.150 nanoamperes (not shown), at which point a test voltage of zero millivolts is applied between second working electrode 214 and reference electrode 10. Reaction period $t_R$ is typically from about 2 to about 4 seconds after initiation of the measuring and is more typically about 3 seconds after initiation of the measuring, i.e., after $t_1$. In exemplary step 330, after reaction period $t_R$, the test voltage in the subject method is applied to test strip 200 at $t_1$ for a total test time $t_T$. In an alternative method (not shown), the reaction period $t_R$ is omitted such that the start of the test commences as soon as sufficient current is flowing through second working electrode 214.

Figure 7:
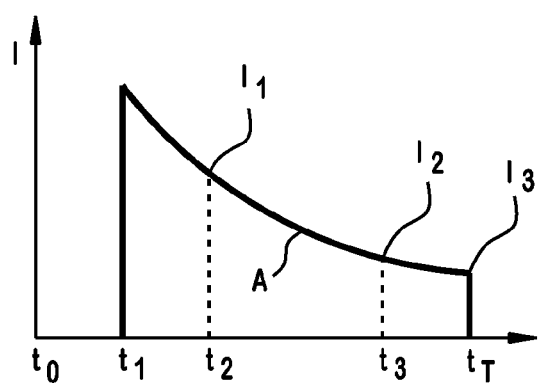
FIG. 7 illustrates an exemplary embodiment of a chart showing test currents generated when the test voltages of FIG. 6 are applied to the test strip.

FIG. 7 is an exemplary chart of a current transient A (i.e., the measured electrical current response in nanoamperes as a function of time) that is measured when the test voltage of FIG. 6 is applied to test strip 200. Test currents $I_i$ obtained from current transients A are generally indicative of the analyte concentration in the sample as will be described in exemplary step 350 below. Referring to FIGS. 6 and 7, in exemplary step 340, after the test voltage is applied between second working electrode 214 and reference electrode 210 at time $t_1$, a first test current $I_1$, a second test current $I_2$, and a third (or end) test current $I_3$ are measured at times $t_2$, $t_3$ and $t_T$, respectively. The test voltage applied between second working electrode 214 and reference electrode 210 is generally from about +100 millivolts to about +600 millivolts. In one embodiment in which second working electrode 214 is carbon ink and the mediator is ferricyanide, the test voltage is about +400 millivolts. Other mediator and electrode material combinations will require different test voltages. The duration of first test voltage is generally from about 4 and 6 seconds after a reaction period and is typically about 5 seconds after a reaction period. Typically, time $t_i$ is measured relative to time $t_1$. In practice, each test current $I_i$ is the average of a set of measurements obtained over a short interval, for example, five measurements obtained at 0.01 second intervals starting at $t_{i+1}$, where I ranges from 1 to 3.

Referring to FIG. 5A in exemplary step 350, a hematocrit-corrected glucose concentration may be determined with the following:

$$G = \frac{\left[\left(\frac{I_1}{I_2}\right)^p I_3\right] - \text{intercept1}}{\text{slope1}} \quad (1)$$

where:

G is the hematocrit-corrected glucose concentration;
$I_1$ is the first test current;
$I_2$ is the second test current;
$I_3$ is the third test current;
p is a power term that determines the strength of the hematocrit correction: the greater the magnitude of p, the greater the hematocrit correction, i.e., the larger is the term $$\left(\frac{I_1}{I_2}\right)$$

in Equation 1;

intercept1 is an intercept value determined from a linear regression of a plot of $$\left[\left(\frac{I_1}{I_2}\right)^p I_3\right]$$

versus a reference glucose concentration; and slope1 may be a slope value determined from a linear regression of a plot of $$\left[\left(\frac{I_1}{I_2}\right)^p I_3\right]$$

versus the reference glucose concentration.

In one embodiment, first test current $I_1$ may be from about 3 seconds after a reaction period to about 4 seconds after a reaction period t1, second test current $I_2$ may be from about 4 seconds after a reaction period t1 to about 5 seconds after a reaction period t1, and third test current $I_3$ may be about 5 seconds after a reaction period t1. In one embodiment, first test current $I_1$ may be measured at a time at which signal noise is low. For plasma treated test strip, the first test current may be measured at about 3.5 seconds, the second test current may be measured at about 4.5 seconds and the third test current at about 5 seconds. For untreated test strip, the first current may be measured at about 4 seconds; the second test current at about 4.5 seconds; and the third test current at about 5 seconds.

In one embodiment, power term p depends on a threshold value of first test current $I_1$ and may be from about one to about four. If first test current $I_1$ is above the threshold value, then Equation 1 is used to calculate the hematocrit-corrected glucose concentration G. If first test current $I_1$ is at or below the threshold value, then power term p may be set to zero in Equation 1 and the term $$\left(\frac{I_1}{I_2}\right)^p$$

becomes one. In one embodiment, the threshold value of first test current $I_1$ may be from about 4 microamperes to about 7 microamperes.

In another embodiment, power term p comprises a value obtained with the following:

$$p = a - \frac{b}{I_3} \qquad (2)$$

where a is a first tuning parameter and b is a second tuning parameter.

By subtracting the inverse of $I_3$ from first tuning parameter a, power term p is increased for large values of $I_3$ and is reduced for low values of $I_3$, corresponding to high and low glucose concentrations, respectively. In one embodiment, each of first and second tuning parameters a and b is from about zero to about five. For low glucose values, e.g., less than about 75 mg/dL, the value of p is preferably about 1 while for other glucose values, the value of p can be from about 1.5 to about 3.5. In exemplary step 340, the hematocrit-corrected glucose concentration may then be displayed on meter 102.

Referring to FIG. 5B, a method 400 for determining batch-specific first and second tuning parameters a and b will now be described. In exemplary step 410, a plurality of combinations of first and second tuning parameters a and b are provided. In an embodiment in which each of the first and second tuning parameters may vary from about zero to about five in increments of 0.1, a total of 2601 tuning parameter combinations are possible. In exemplary step 420, a first power term p1 for a first combination of the first tuning parameter and the second tuning parameter may be determined with Equation 3.

In exemplary step 430, a hematocrit-corrected current for each of a plurality of samples tested with the batch of test strips may be determined with the following:

$$I_{corrected} = \left(\frac{I_1}{I_2}\right)^{p1} * I_3 \qquad (3)$$

where $I_{corrected}$ is a hematocrit-corrected current and p1 is the first power term.

In exemplary step 440, a slope2 and an intercept2 is determined from a linear regression of a plot of hematocrit-corrected current versus a reference plasma glucose concentration.

In exemplary step 450, a hematocrit-corrected glucose concentration is determined for each of the plurality of samples with the following:

$$G_{corrected} = \frac{I_{corrected} - \text{intercept2}}{\text{slope2}} \qquad (4)$$

where:
$G_{corrected}$ is a hematocrit-corrected glucose concentration;
intercept2 is the intercept value determined from a linear regression of a plot of $I_{corrected}$ versus a reference glucose concentration $G_{reference}$; and
slope2 is the slope value determined from a linear regression of a plot of $I_{corrected}$ versus a reference glucose concentration;

In exemplary step 460, a bias for each of the hematocrit-corrected glucose concentrations is determined with equations of the form:

$$Bias_{abs} = G_{corrected} - G_{reference} \text{ for } G_{reference} \text{ less than 75 mg/dL and} \qquad (5)$$

$$Bias_{\%} = \frac{(G_{corrected} - G_{reference})}{G_{reference}} \text{ for } G_{reference} \geq \text{ to 75 mg/dL} \qquad (6)$$

where:
$Bias_{abs}$ is an absolute bias;
$Bias_{\%}$ is a percent bias;
$G_{corrected}$ is defined above for Equation 4; and
$G_{reference}$ is the reference glucose concentration;

In exemplary step 470, an accuracy for the first combination of the first and second tuning parameters is determined with the following:

$$\text{Accuracy} = \frac{n15}{n} * 100 \qquad (7)$$

where:
n15 is the number of data points within a bias criteria; and
n is the total number of data points;

In exemplary step 480, a hematocrit slope is determined from a linear regression of a plot of the bias versus the percent hematocrit.

In exemplary step 490, a standard deviation of the bias (which may be a mean bias) is determined with the following:

$$s = \left(\frac{1}{n-1}\sum_{i=1}^{n}(x_i - \bar{x})^2\right)^{1/2} \qquad (8)$$

where:
s is the standard deviation;
n is the number of samples;
$x_i$ is the sample; and
$\bar{x}$ is the mean of the sample.

The standard deviation of the bias (which may be a mean bias) is a measure of the noise introduced by the set of instructions.

In exemplary step 500, the previous steps for all combinations of the first and second tuning parameters are repeated. In exemplary step 510, a surface plot 800 (FIG. 8) of the accuracy calibration space for all combinations of first tuning parameter a and second tuning parameter b is generated. A region 802 of acceptable accuracy may be determined from the accuracy calibration space. The region 802 indicates an area of greatest accuracy, approximately ±15% or about 12 mg/dL for accuracy requirement. The data generated by plot 800 is calculated from a batch of plasma treated carbon type test strip. In one embodiment, a minimum accuracy of 95% is used as an acceptance criterion.

In exemplary step 520, a surface plot 900 (FIG. 9) of the hematocrit slope calibration space for all combinations of first tuning parameter a and second tuning parameter b is determined. A maximum negative hematocrit slope may then be determined from the hematocrit slope calibration space. In one embodiment, the hematocrit slope acceptance criterion is greater than −0.6% bias per % hematocrit, which is indicated by region 902 in plot 900.

Figure 10:
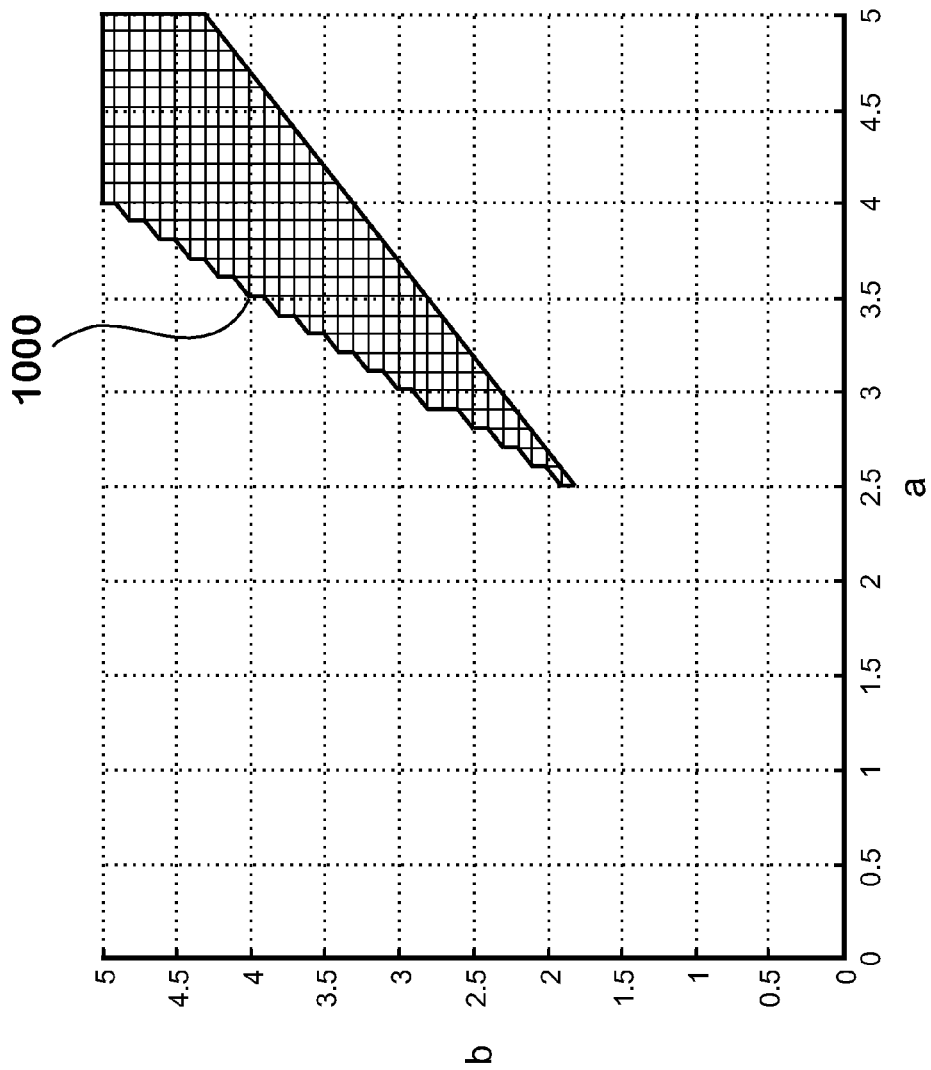
FIG. 10 illustrates an exemplary embodiment of a combined surface plot for all combinations of the first and second tuning parameters which meet an accuracy and hematocrit slope acceptance criteria and using the data in FIGS. 8 and 9.

In exemplary step 530, a combined surface plot 1000 (FIG. 10) of both the accuracy calibration space and the hematocrit slope calibration space for all combinations of first tuning parameter a and second tuning parameter b is determined.

Figure 8:
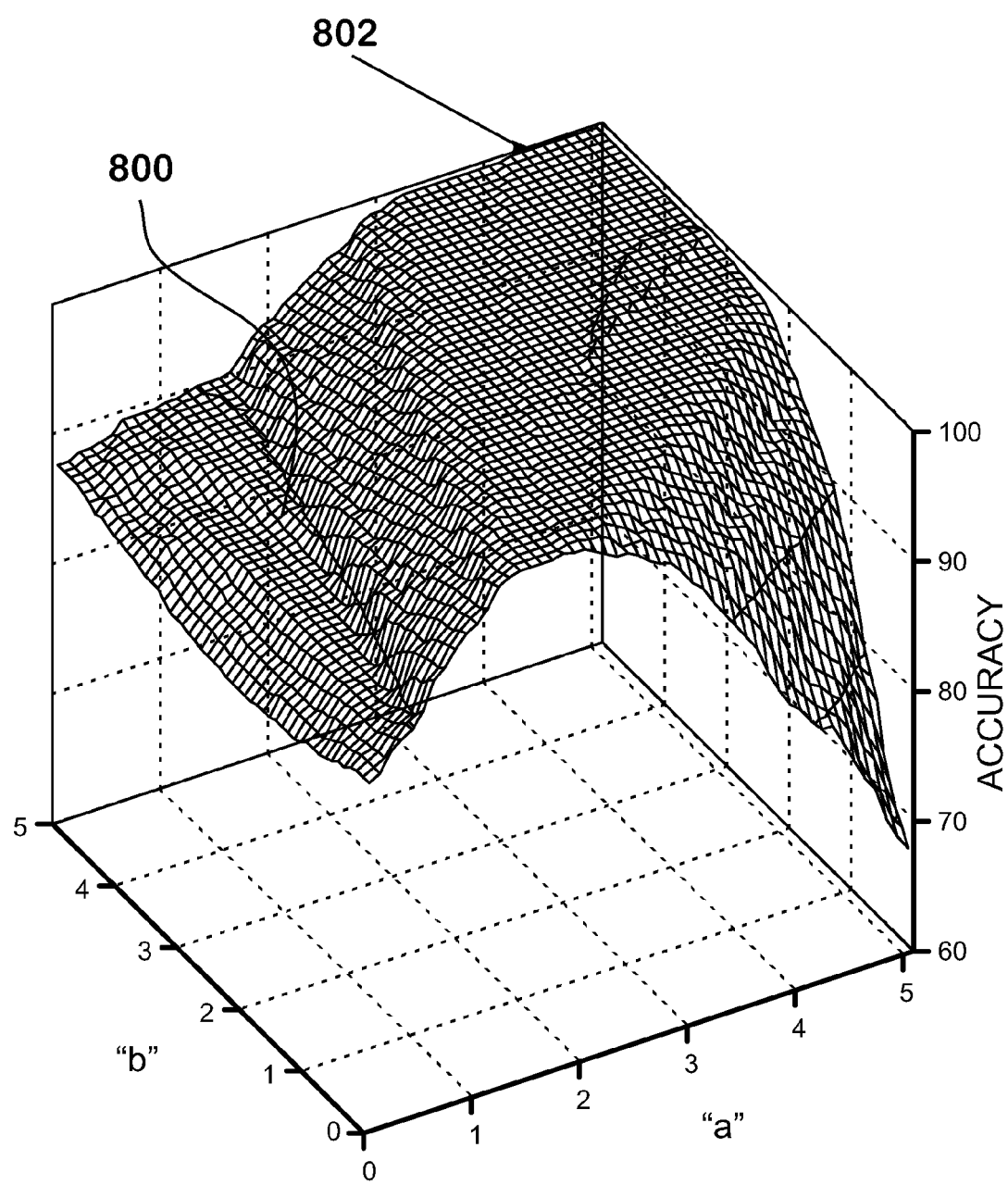
FIG. 8 illustrates an exemplary embodiment of a surface plot of the accuracy calibration space for all combinations of the first tuning parameter and the second tuning parameter for a batch of test strips having the embodiment shown in FIGS. 2 and 3.
Figure 9:
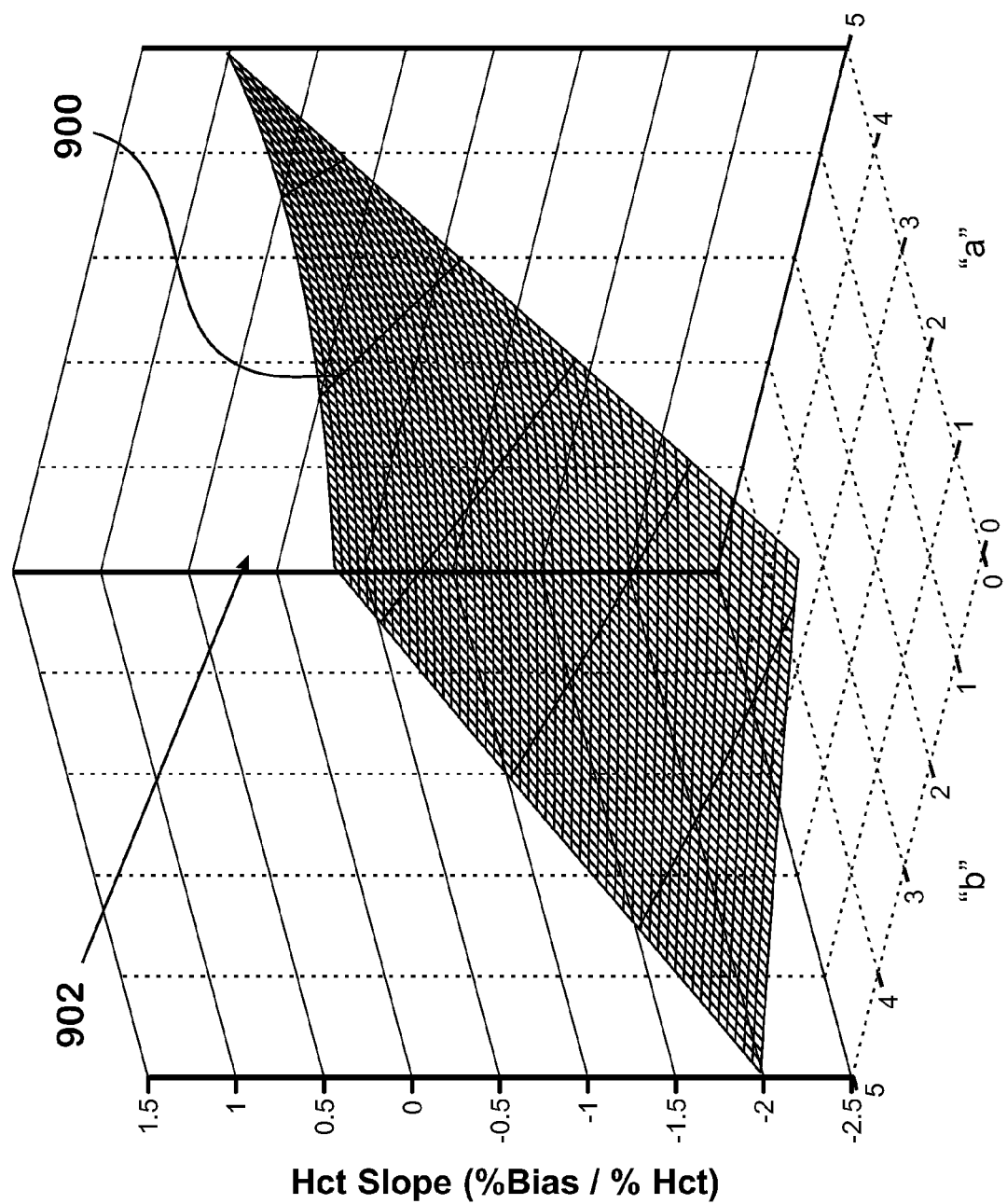
FIG. 9 illustrates an exemplary embodiment of a surface plot of the hematocrit slope calibration space for all combinations of the first tuning parameter and the second tuning parameter for a batch of test strips having the embodiment shown in FIGS. 2 and 3.

In exemplary step 540, the batch-specific first tuning parameter and second tuning parameter is determined from the region in the combined surface plot in which the acceptance criteria for both accuracy and hematocrit slope are met. In one embodiment, the acceptance criterion for accuracy is greater than 95% and the hematocrit slope acceptance criterion is greater than −0.5% bias per % hematocrit. The batch-specific first and second tuning parameters may then be used to determine a set of batch-specific calibration parameters, e.g., slope and intercept, by repeating steps 420, 430 and 440 in method 400. To use the same set of tuning parameters for multiple batches of test strips, a set of tuning parameters may be determined for each batch by method 400 and then regions of overlap in the combined accuracy and hematocrit calibration space for all the batches may be determined. That is, combinations which pass suitable criteria (e.g., with accuracy is greater than 95% and the slope greater than −0.6% bias per % hct) in FIGS. 8 and 9 are retained. The resulting calibration space is illustrated by the elevated region in FIG. 10.

EXAMPLE

Determination of Hematocrit-Corrected Glucose Concentration with a Test Strip as Shown in FIGS. 2 and 3

A batch of test strips was tested with 432 whole blood samples having at least three different glucose concentrations (i.e., 55 mg/dL, 240 mg/dL and 450 mg/dL) and hematocrit levels ranging from 30 to 55%. The hematocrit-corrected glucose concentration was determined for each data point in the data mapping as described previously with methods 300 and 400. A surface plot 800 of the accuracy calibration space for all combinations of tuning parameters a and b was determined and is illustrated in FIG. 8. The elevated region 802 in the center of the surface plot indicates the area of acceptable accuracy, e.g., greater than 95% of the values within an International Standards Organization (ISO) bias requirement of about +/−15% for glucose values greater than or equal to about 75 mg/dL or about 12 mg/dL for glucose values less than about 75 mg/dL.

A surface plot 900 of the hematocrit slope calibration space for all combinations of tuning parameters a and b was also determined and is shown in FIG. 9 for glucose concentration greater than about 100 mg/dL and less than about 300 mg/dL because it is believed that this range is the most resistant to hematocrit correction. The region 902 in the center of the plot meets the acceptance criteria for the hematocrit slope of greater than about −0.6% bias per % hematocrit.

FIGS. 8 and 9 illustrate a large calibration space that characterizes the effect of all 2061 possible combinations of the tuning parameters on accuracy and hematocrit slope. Visualizing the data in this manner provides a method for reducing this large calibration space into a useful set of tuning parameters. FIG. 8 suggests where there is a region (e.g., 802) of accuracy within the acceptance criteria. This region 802 may be reduced further by considering the hematocrit slope along with the accuracy. This may be achieved by setting acceptance criteria for both the accuracy and hematocrit slope at each combination of tuning parameters. Using an accuracy requirement of greater than 95% of the data within the ISO bias limits of +/−15% for glucose values greater than or equal to 75 mg/dL or 12 mg/dL for glucose values less than 75 mg/dL (FIG. 8) and a hematocrit requirement of greater than −0.6% bias per % hematocrit (FIG. 9), a calibration space 1000 may determined, as illustrated by the shaded region in FIG. 10. The calibration space can be reduced by using more narrow acceptance criteria, e.g., by increasing the required accuracy and by reducing the allowed hematocrit slope which results in a smaller set of batch-specific tuning parameters.

Once the preferred set of tuning parameters a and b are obtained from the data mapping, they can be applied to the data set and the above is repeated to determine the slopes and intercepts for the hematocrit compensated currents and the reference glucose values. The tuning and calibration parameters are now set for this batch. When dealing with multiple batches, all of the steps should be repeated for each individual batch, and areas in the calibration space which allow the same set of tuning parameters to be used should be found (e.g. by creating FIG. 10 for each batch and looking for areas of overlap).

Figure 11A:
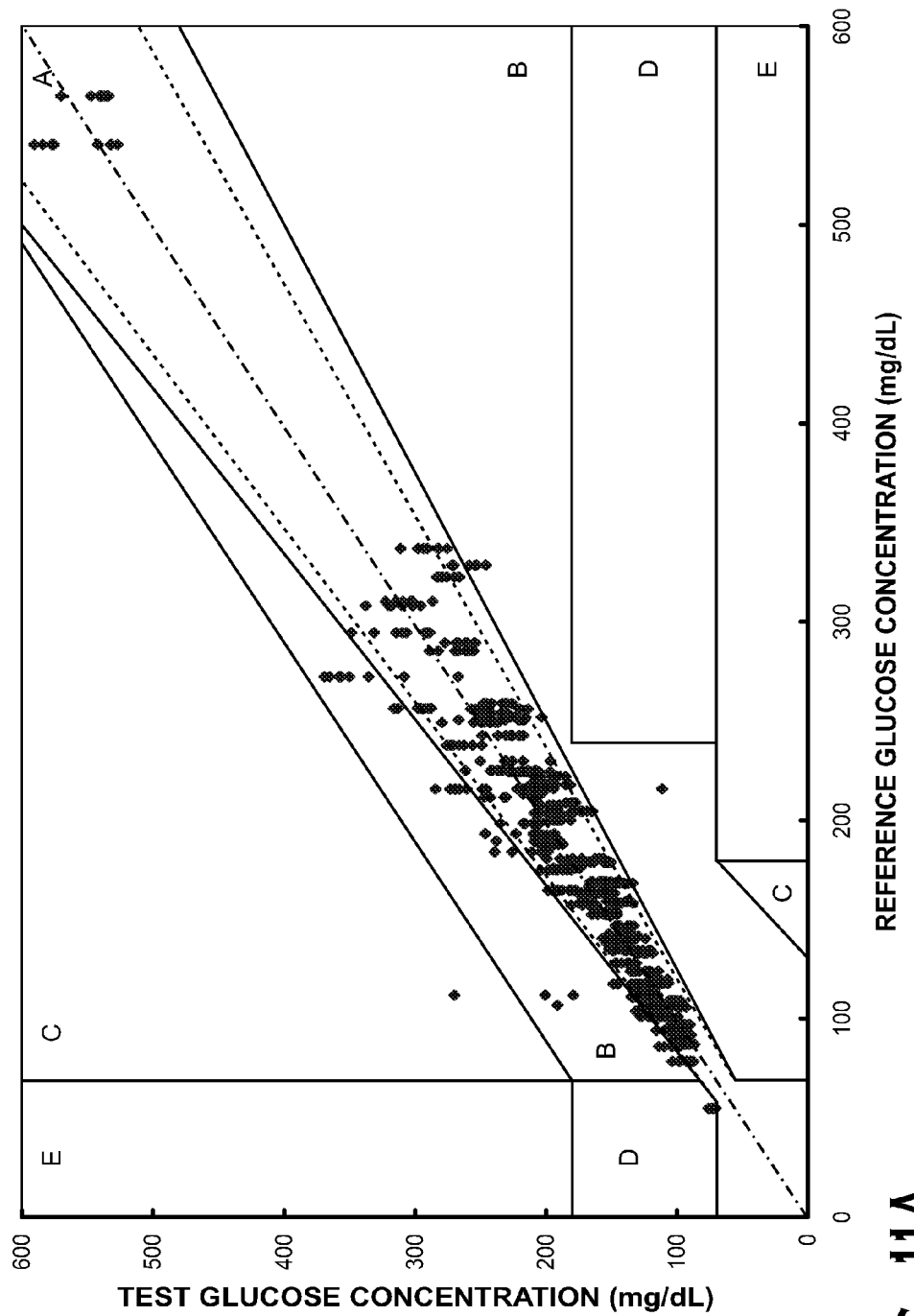
FIGS. 11A and 11B illustrate Clarke Error Grid analysis showing test glucose concentration plotted as a function of reference glucose concentration prior to and after applying an exemplary embodiment to the test data, respectively. The test data was obtained with a batch of test strips having the embodiment shown in FIGS. 2 and 3.
Figure 11B:
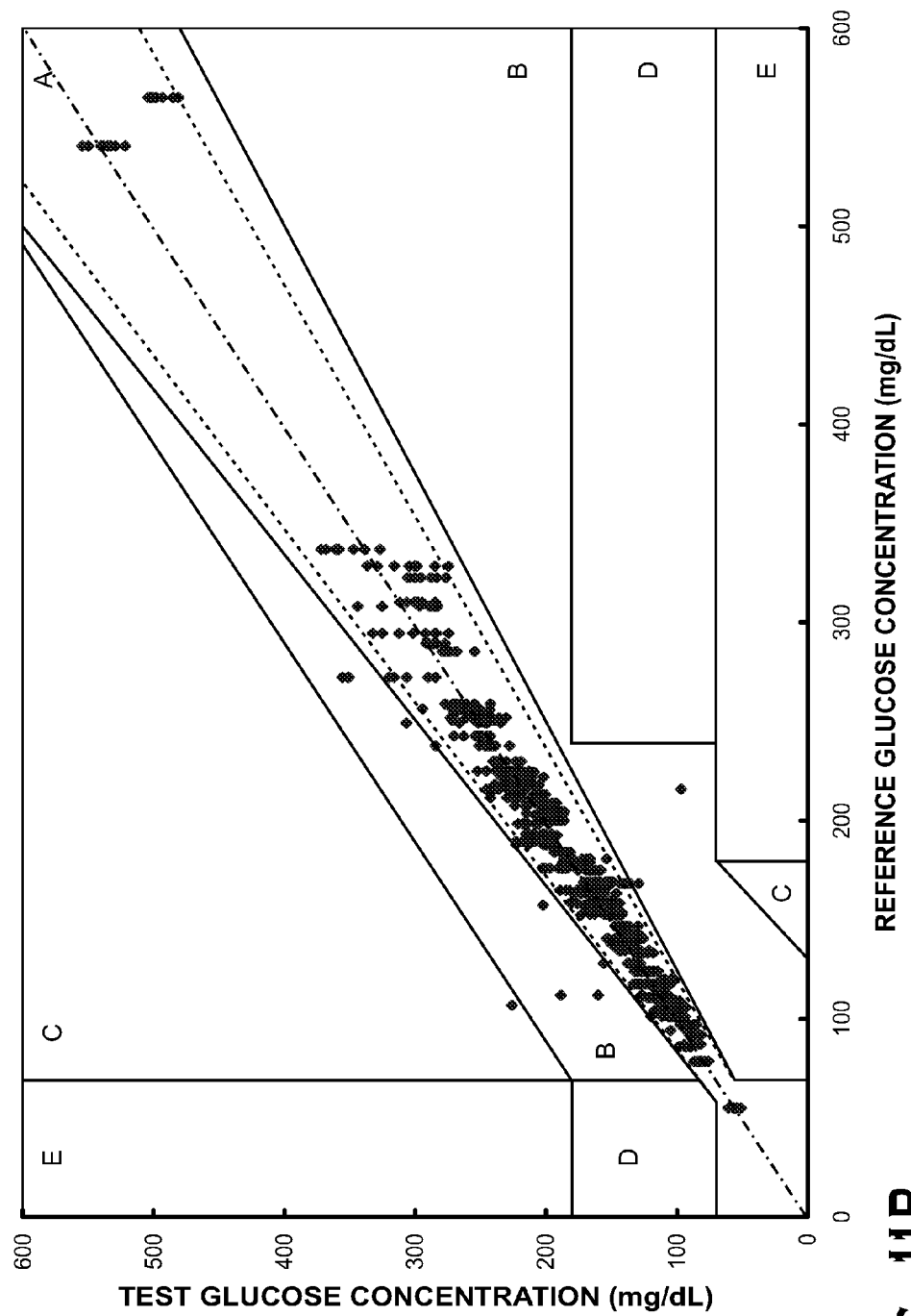

FIGS. 11A and 11B illustrate Clarke Error Grid plots of test glucose concentration as a function of reference glucose concentration as determined on a reference instrument. A Clark's Error Grid analysis provides a method to access the clinical accuracy of a blood glucose monitoring device. The error grid of such an analysis categorizes a device's response against a reference value into one of five clinical accuracy zones (i.e., zones A-E). Zone A indicates clinically accurate results; zone B indicates results that are not clinically accurate but pose minimal risk to patient health; and zones C through E indicate clinically inaccurate results that pose increasing potential risk to patient health (see Clarke, William L. et al., *Evaluating Clinical Accuracy of Systems for Self Monitoring of Blood Glucose*, Diabetes Care, Vol. 10 No. 5, 622-628 [1987], which is incorporated by reference as if set forth herein). Specifications can be developed based on the percent of results falling within the various error grid zones. In the current example, it is desirable that at least 95% of the data lie within zone A and the rest of the data lie within zone B. FIG. 11A illustrates uncorrected data from the given batch of test strips tested with 432 whole blood samples. FIG. 11B illustrates the same set of data but with the hematocrit-correction of the subject method applied to the data described previously in methods 300 and 400. A summary of the percent of data falling within each zone is given in Table 1 below for uncorrected data and corrected data.

TABLE 1

Summary of Clarke Error Grid Analysis

| Zone | Percent within Zone for Uncorrected Data | Percent within Zone for Corrected Data |
|---|---|---|
| A | 92.2 | 98.6 |
| B | 6.7 | 1.2 |
| C | 0.1 | 0.1 |
| D | 0.9 | 0.0 |
| E | 0.0 | 0.0 |

The data in Table 1 illustrates an increase in the percent of data points in Zone A when the subject method is used to correct the data for the hematocrit effect.

The data may also be presented as a percent falling within different ISO bias criteria, as illustrated in Table 2 below. Steps 410-470 of method 400 were used to determine the percent within each bias criteria.

TABLE 2

Summary of Bias Results

| ISO Bias Criteria (%) | Percent within Bias Criteria for Uncorrected Data | Percent within Bias Criteria for Corrected Data |
| --- | --- | --- |
| +/−20 | 92.3 | 98.6 |
| +/−15 | 83.7 | 97.1 |
| +/−10 | 66.3 | 85.4 |

The data in Table 2 indicates an increase in the percent of data falling within each ISO bias criteria when the subject method is used to correct the data for the hematocrit effect.

Figure 11C:
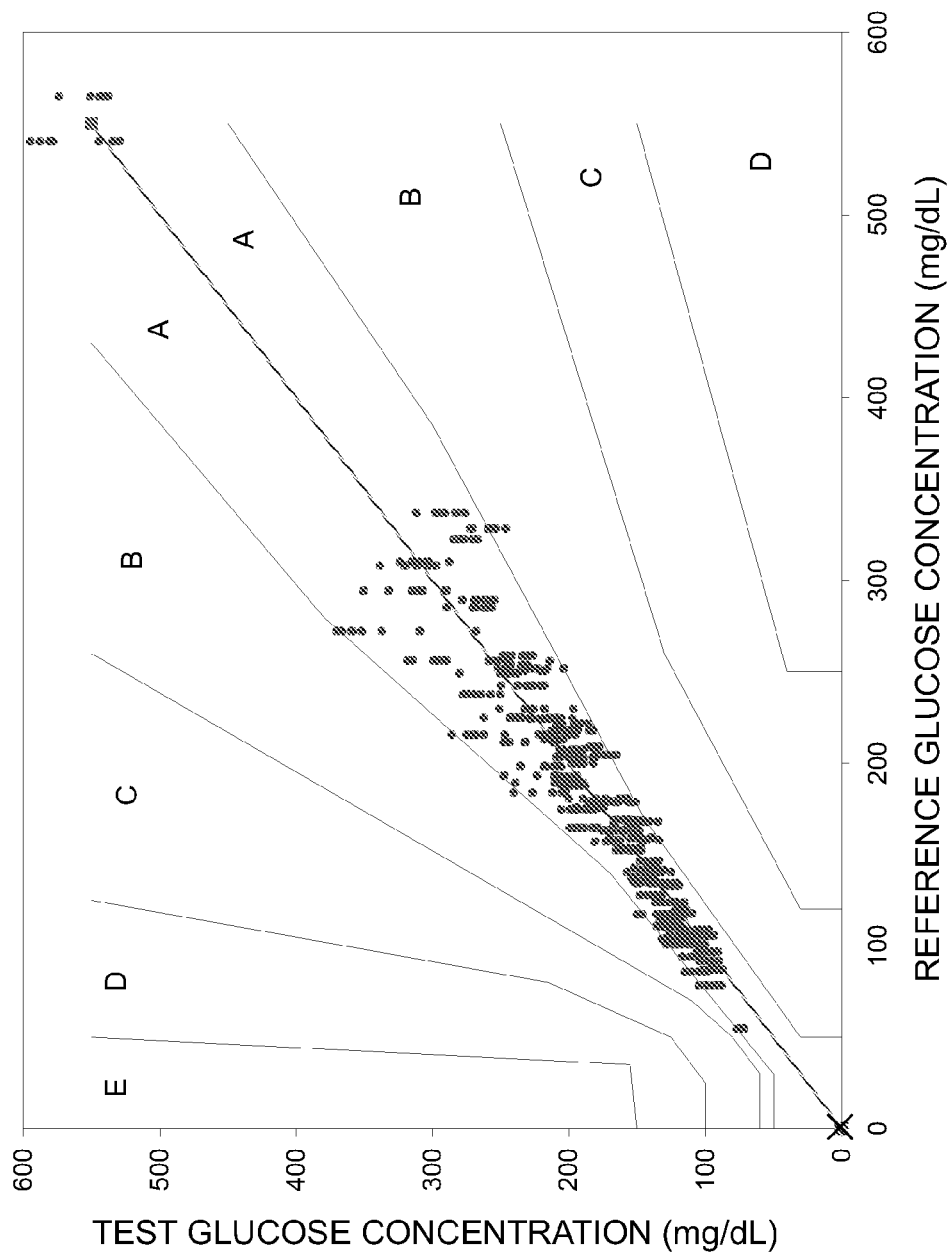
FIGS. 11C and 11D illustrate Parkes Error Grid analysis showing test glucose concentration plotted as a function of reference glucose concentration prior to and after applying an exemplary embodiment to the test data, respectively. The test data in FIGS. 11A and 11B was used along with additional data and after applying a suitable error trapping.
Figure 11D:
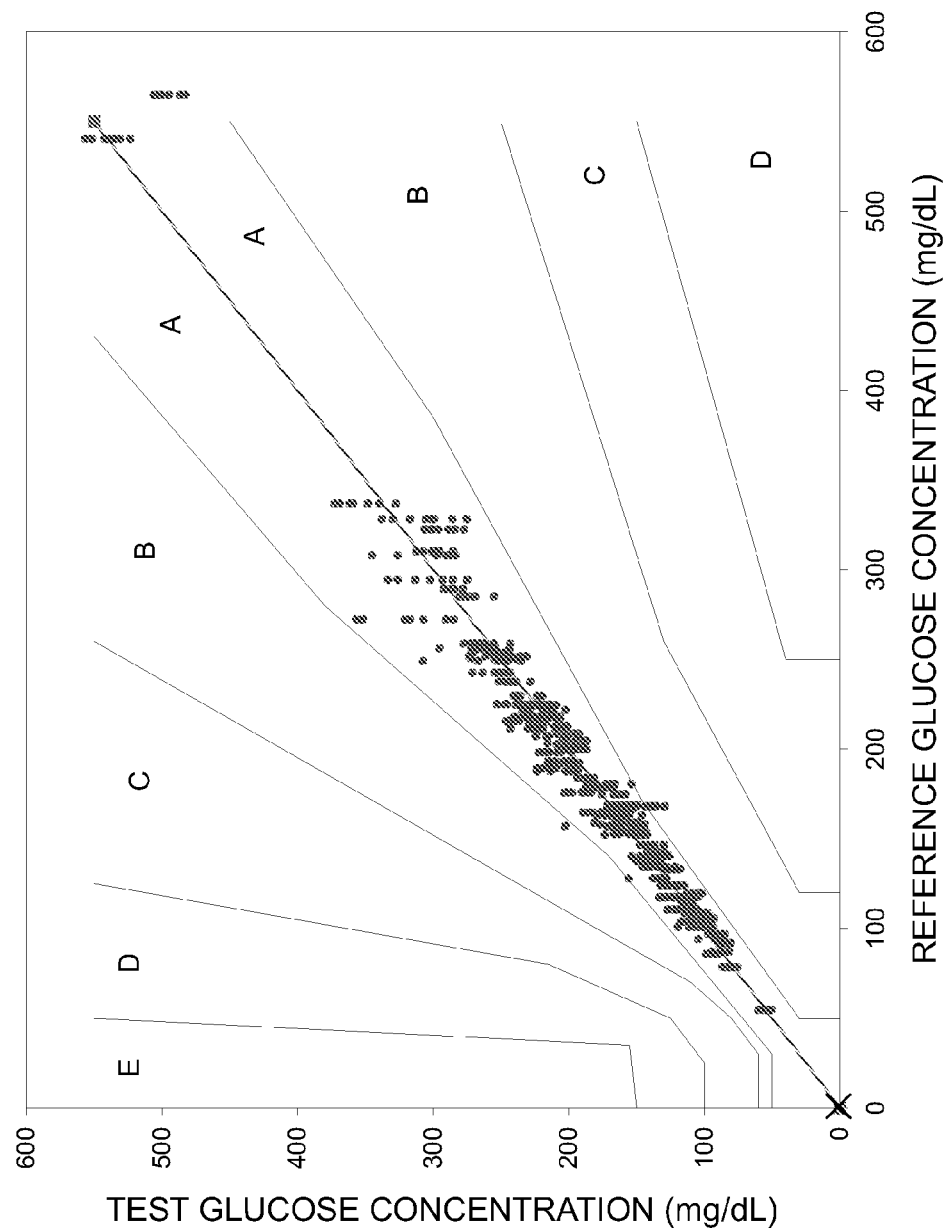

FIGS. 11C and 11D illustrate Parkes Error Grid plots of the same data as shown in FIGS. 11A and 11B with error trapping to remove outliers. The Parkes Error Grid is a successor to the Clarke Error Grid and differs from the latter (a) in representing a consensus of a larger number of physicians and (b) in changing risk boundaries based on advances in knowledge acquired since the original publication of Clarke, et al. (see Parkes, Joan L. et al., *A New Consensus Error Grid to Evaluate the Clinical Significance of Inaccuracies in the Measurement of Blood Glucose*, Diabetes Care, Vol. 23 No. 8, 1143-1147 [2000]). The Parkes Error Grid eliminates the discontinuities of risk levels (i.e., skipping risk categories in crossing from one zone boundary to another) of the Clarke Error Grid.

FIG. 11C illustrates uncorrected data from the given batch of test strips tested with 761 whole blood samples and with outliers removed by error trapping. FIG. 11D illustrates the same set of data as in FIG. 11C but with the hematocrit-correction of the subject method applied to the data described previously in methods 300 and 400. It is desirable that at least 95% of the data lie within zone A and the rest of the data lie within zone B. A summary of the percent of data falling within each zone is given in Table 3 below for uncorrected data and corrected data.

TABLE 3

Summary of Parkes Error Grid Analysis

| Zone | Percent within Zone for Uncorrected Data | Percent within Zone for Corrected Data |
| --- | --- | --- |
| A | 96.8 | 99.2 |
| B | 3.2 | 0.8 |
| C | 0.0 | 0.0 |
| D | 0.0 | 0.0 |
| E | 0.0 | 0.0 |

The data in Table 3 illustrates an increase in the percent of data points in Zone A when the subject method is used to correct the data for the hematocrit effect.

In conclusion, the system and methods described and illustrated herein can be used to determine a hematocrit-corrected glucose concentration. Thus, the glucose result obtained with the exemplary subject system and method is believed to be more accurate.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method for determining a glucose concentration measurable with a system having a test strip and a meter, the method comprising:

applying a test voltage between a reference electrode and a working electrode coated with a reagent layer disposed on a matrix layer having a mediator;

measuring a first test current, a second test current and a third test current at the working electrode with the meter after a blood sample containing an analyte is applied to the test strip to physically transform the analyte into an enzymatic by-product;

determining a glucose concentration from the first, second and third test currents, in which the glucose concentration comprises a value obtained with the following:

$$G = \frac{\left[\left(\frac{I_1}{I_2}\right)^p I_3\right] - \text{intercept1}}{\text{slope1}}$$

where:

G comprises the glucose concentration;
$I_1$ comprises the first test current;
$I_2$ comprises the second test current;
$I_3$ comprises the third test current;
p comprises a power term that depends on of the third test current in which the power term p comprises a value obtained with the following:

$$p = a - \frac{b}{I_3}$$

where a comprises a first tuning parameter between 2.5 and 5 and b comprises a second tuning parameter between 1.75 and 5;

intercept1 comprises an intercept value determined from a linear regression of a plot of $$\left[\left(\frac{I_1}{I_2}\right)^p I_3\right]$$

versus a reference glucose concentration for a batch of test strips; and slope1 comprises a slope value determined from a linear regression of a plot of $$\left[\left(\frac{I_1}{I_2}\right)^p I_3\right]$$

versus the reference glucose concentration for the particular batch of test strip; and displaying the glucose concentration.

2. The method of claim 1, in which the threshold value of the first test current comprises from about 5 microamperes to about 7 microamperes.

3. The method of claim 1, in which the power term comprises a value from about one to about four.

\* \* \* \* \*